United States Patent
Vitali et al.

(10) Patent No.: US 8,937,152 B2
(45) Date of Patent: Jan. 20, 2015

(54) NON-SELECTIVE SOMATOSTATIN ANALOGUES

(75) Inventors: Andrea Vitali, Milan (IT); Massimo Pinori, Paderno D'adda (IT); Paolo Mascagni, Villasanta (IT)

(73) Assignee: Italfarmaco SpA, Milan (IT)

( * ) Notice: Subject to any disclaimer, the term of this patent is extended or adjusted under 35 U.S.C. 154(b) by 355 days.

(21) Appl. No.: 12/734,475

(22) PCT Filed: Nov. 24, 2008

(86) PCT No.: PCT/EP2008/066081
§ 371 (c)(1),
(2), (4) Date: Jun. 4, 2010

(87) PCT Pub. No.: WO2009/071460
PCT Pub. Date: Jun. 11, 2009

(65) Prior Publication Data
US 2010/0323964 A1  Dec. 23, 2010

(30) Foreign Application Priority Data

Dec. 3, 2007 (IT) .............................. MI2007A2266
Dec. 7, 2007 (EP) .................................... 07425778

(51) Int. Cl.
| A61K 38/31 | (2006.01) |
| C07K 7/64 | (2006.01) |
| A61K 38/04 | (2006.01) |
| C07K 14/655 | (2006.01) |

(52) U.S. Cl.
CPC ........... *C07K 14/655* (2013.01); *C07K 14/6555* (2013.01)
USPC ........................... 530/311; 530/329; 514/11.1

(58) Field of Classification Search
None
See application file for complete search history.

(56) References Cited

U.S. PATENT DOCUMENTS

| 6,225,284 B1 * | 5/2001 | Albert et al. .................. 514/11.1 |
| 2001/0021519 A1 | 9/2001 | Liu et al. |
| 2005/0014686 A1 * | 1/2005 | Albert et al. ..................... 514/10 |
| 2006/0052289 A1 * | 3/2006 | Bruns et al. ........................ 514/9 |
| 2006/0270730 A1 * | 11/2006 | Katopodis ..................... 514/419 |
| 2010/0323964 A1 * | 12/2010 | Vitali et al. .................. 514/11.1 |

FOREIGN PATENT DOCUMENTS

| EP | 1 598 366 A * | 11/2005 | ........... C07K 14/655 |
| EP | 1 598 366 A1 | 11/2005 | |
| EP | 1787658 * | 5/2007 | |
| WO | 97/01579 A * | 1/1997 | ........... C07K 14/655 |
| WO | WO 97/01579 A2 | 1/1997 | |
| WO | WO 02/10192 A2 | 2/2002 | |
| WO | WO 03/080855 A2 | 10/2003 | |
| WO | WO 2005000893 | * 1/2005 | |
| WO | WO 2005/014624 A2 | 2/2005 | |
| WO | WO 2005034989 | * 4/2005 | |
| WO | WO 2005053732 | * 6/2005 | |
| WO | WO 2006/066868 A2 | 6/2006 | |

OTHER PUBLICATIONS

Chruscinska E et al: "Unusual gain in the coordination ability of vasopressin-like peptides towards Ca2+ ions by insertion of the highly hydrophobic side chain" New Journal of Chemistry 20030201GB, vol. 27, No. 2, Feb. 1, 2003, pp. 251-256, XP002496704, ISSN: 1144-0546, Figure I.*
Kostenich et al: "Targeting small-cell lung cancer with novel fluorescent analogs of somatostatin"; Lung Cancer, Elsevier, Amsterdam, NL; vol. 50, No. 3, Dec. 1, 2005; pp. 319-328, XP005160237; ISSN: 0169-5002.*
http://en.wikipedia.org/wiki/Pasireotide (Jun. 18, 2013).*
Chruscinska, E., et al; "Unusual gain in the coordination ability of vasopressin-like peptides towards $Cu^{2+}$ ions by insertion of the highly hydrophobic side chain"; *New Journal of Chemistry*; vol. 27, No. 2; pp. 251-256 (2003) XP-002496704.
Kostenich, G., et al; "Targeting small-cell lung cancer with novel fluorescent analogs of somatostatin"; *Lung Cancer*; vol. 50, No. 3; pp. 319-328 (2005) XP-005160237.
de Herder, W.W., et al; "Somatostatin receptors in gastroenteropancreatic neuroendocrine tumours"; *Endocrine-Related Cancer*, vol. 10; pp. 451-458 (2003).
Schmid, H.A., et al; "Functional Activity of the Multiligand Analog SOM230 at Human Recombinant Somatostatin Receptor Subtypes Supports Its Usefulness in Neuroendocrine Tumors"; *Neuroendocrinology*; vol. 80(suppl 1):47-50 (2004).
Synthesis; *Communications*; Georg Thieme Verlag, Stuttgart, New York, 3 pgs. (1983).
Janecka, A., et al; "Review, Somatostatin analogs"; *J. Peptide Res.*, vol. 58, pp. 91-107 (2001).
Weckbecker, G., et al; "Opportunities in Somatostatin Research: Biological, Chemical and Therapeutic Aspects"; *Nature Reviews / Drug Discovery*; vol. 2, pp. 999-1017 (2003).
Zatelli, M.C., et al; "Somatostatin Receptor Subtype 1 Selective Activation in Human Growth Hormone (GH)- and Prolactin (PRL)-Secreting Pituitary Adenomas: Effects on Cell Viability, GH, and PRL Secretion"; *The Journal of Clinical Endocrinology & Metabolism*; vol. 88, No. 6, pp. 2797-2802 (2003).

(Continued)

*Primary Examiner* — Maury Audet
(74) *Attorney, Agent, or Firm* — Nixon & Vanderhye P.C.

(57) ABSTRACT

Cyclohexapeptides of formula (I):

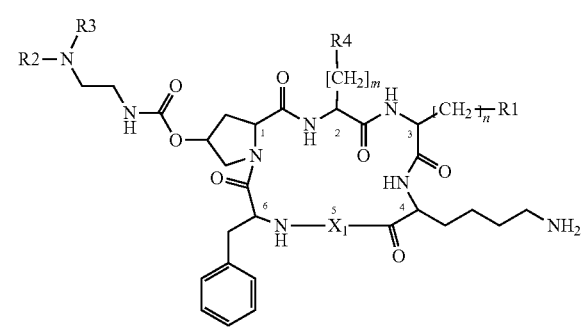

as defined herein. The cyclohexapeptides are non-selective functional analogs of somatostatin.

31 Claims, No Drawings

(56) References Cited

OTHER PUBLICATIONS

Zatelli, M.C., et al; "Evidence for Differential Effects of Selective Somatostatin Receptor Subtype Agonists on α-Subunit and Chromogranin A Secretion and on Cell Viability in Human Nonfunctioning Pituitary Adenomas in Vitro"; *The Journal of Clinical Endocrinology & Metabolism*; vol. 89, No. 10, pp. 5181-5188 (2004).

van der Hoek, J., et al; "Novel Subtype Specific and Universal Somatostatin Analogues: Clinical Potential and Pitfalls"; *Current Pharmaceutical Design*, vol. 11, pp. 1573-1592 (2005).

Hirst, B.H., et al; "Structure-Activity Studies with Somatostatin: The Role of Tryptophan in Position 8"; *Regulatory Peptides*, vol. 1, pp. 97-113 (1980).

"*Proceedings of the Twelfth American Peptide Symposium; Peptides Chemistry and Biology*"; Edited by John A. Smith and Jean E. River; Eighth Alan E. Pierce Award Lecture; Dr. Daniel F. Veber; 20 pgs (1992).

Erchegyi, J., et al; "Somatostatin Receptor 1 Selective Analogues: 2. $N^{\alpha l}$-Methylated Scan"; *J. Med. Chem.*, vol. 48, pp. 507-514 (2005).

Okarvi, S.M.; "Peptide-Based Radiopharmaceuticals: Future Tools for Diagnostic Imaging of Cancers and Other Diseases"; *Medicinal Research Reviews*; vol. 24, No. 3, pp. 357-397 (2004).

Weiner, R.E., et al; "Radiolabeled Peptides in Oncology"; *Biodrugs*, vol. 19, No. 3, pp. 145-163 (2005).

Vela, M.A., et al; "Synthesis of 1- and 2-Naphthol Analogues of DL-Tyrosine. Potential Fluorescent Probes of Peptide Structure and Dynamics in Complex Environments"; *J. Org. Chem.*, vol. 55, pp. 2913-2918 (1990).

Sabat, M., et al; "Synthesis of Unnatural Amino Acids via Suzuki Cross-Coupling of Enantiopure Vinyloxazolidine Derivatives"; *Organic Letters*, vol. 2, No. 8, pp. 1089-1092 (2000).

Susini, C., et al; "Rationale for the use of somatostatin analogs as antitumor agents"; *Annals of Oncology*, vol. 17; pp. 1733-1742 (2006).

Ahima, R.S.; "Antagonism of Ghrelin for Glycemic Control in Type 2 Diabetes Mellitus?"; *Endocrinology*, 148(11), pp. 5173-5174 (2007).

Sangiao-Alverellos, S., et al; "Effect of Ghrelin on Glucose-Insulin Homeostatis: Therapeutic Implications"; *International Journal of Peptides*, vol. 2010, Article ID 234709, 25 pgs (2010).

Oberg, K.E.; "The Management of Neuroendocrine Tumors: Current and Future Medical Therapy Options"; *Clinical Oncology*, pp. 1-12 (2011).

Nowland, M.H., et al; "Effects of Short-Term Fasting in Male Sprague-Dawley Rats"; *Comparative Medicine*, vol. 61, No. 2, pp. 138-7 (2011).

Petersenn, S., et al; "Long-term efficacy and safety of subcutaneous pasireotide in acromegaly: results from an open-ended, multicenter, Phase II extension study"; *Pituitary*, The online version of this article (doi: 10.1007/s11102-013-0478-0); Springerlink com; (9 pgs), published online Mar. 26, 2013.

Boscaro, M., et al; "Extended treatment of Cushing's disease with pasireotide: results from a 2-year, Phase II study"; *Pituitary*, The online version of this article (doi: 10.1007/s11102-013-0503-3); Springerlink.com; (7 pgs), published online Aug. 14, 2013.

Petersenn, S., et al; "Pasireotide (SOM230) Demonstrates Efficacy and Safety in Patients with Acromegaly: A Randomized, Multicenter, Phase II Trial"; *J. Clin Endocrin Metab.*, 95(6):000-000 (9 pgs), (2010).

Colao, A., et al; "A 12-Month Phase 3 Study of Pasireotide in Cushing's Disease"; *The New England Journal of Medicine*, 366;10 (11 pgs), (2012).

Wolin, E.M., et al; "Safety, tolerability, pharmacokinetics, and pharmacodynamics of a long-acting release (LAR) formulation of pasireotide (SOM230) in patients with gastroenteropancreatic neuroendocrine tumors: results from a randomized, multicenter, open-label, phase I study"; *Cancer Chemother Pharmacol*; DOI 10.1007/s00280-013-2202-1; Springerlink.com; (9 pgs), published online Jun. 14, 2013.

Schmidt, H.A., et al; "Effects of somatostatin analogs on glucose homeostasis in rats"; *Journal of Endocrinology*, vol. 212, pp. 49-60 (2012).

Boscaro, M., et al; "Treatment of Pituitary-Dependent Cushing's Disease with the Multireceptor Ligand Somatostatin Analog Pasireotide (SOM230): A Multicenter, Phase II Trial"; *JCEM, The Journal of Clinical Endocrinology & Metabolism*; 94:115-122 (2009).

O'Toole, D., et al; "The analysis of quantitative expression of somatostatin and dopamine receptors in gastro-entero-pancreatic tumours opens new therapeutic strategies"; *European Journal of Endocrinology*, 155, pp. 849-857 (2006).

Colao, A., et al; "Supplementary Appendix, Pasireotide in Cushing's Disease—Results from a 12-Month, Phase III Study"; *New England Journal of Medicine manuscript*, 11-05743, (8 pgs), 2012.

Gerhardt, J.; Determination of the Optical Purity of the Amino Acids of peptides and Amino Acid derivatives via GC-MS (A.0.3.); *C.A.T. GmbH & Co, Chromatographie und Analysentechnik KG.*, (3 pgs) 2008.

Briggs, D.I., et al; "A Recent Update on the Role of Ghrelin in Glucose Homeostatis"; *Current Diabetes Review*, vol. 7, pp. 201-207 (2011).

\* cited by examiner

NON-SELECTIVE SOMATOSTATIN ANALOGUES

This application is the U.S. national phase of International Application No. PCT/EP2008/066081 filed 24 Nov. 2008 which designated the U.S. and claims priority to Italian Application No. MI2007A002266 filed 3 Dec. 2007, and European Application No. 07425778.3 filed 7 Dec. 2007, the entire contents of each of which are hereby incorporated by reference.

The present invention relates to new non-selective functional analogue cyclopeptides of somatostatin, to their conjugates and complexes, to processes for the production, to the formulations which contain them and to their uses in the pharmaceutical field.

STATE OF THE ART

Cyclic peptide agonists of somatostatin have been known for some time [J Pept Res 58 (2), 91 (2001)]: in particular, two of these, octreotide and lanreotide, are clinically used for the care of acromegaly and for the symptomatic treatment of carcinomas.

Somatostatin acts through the interaction with 5 receptor subtypes (SSTR1, 2, 3, 4 and 5); but the analogues up to now employed in therapy are nevertheless essentially selective for the single receptor SSTR2.

The great majority of the already known agonists is characterised by the presence, in the peptide structure, of the fragment -DTrp-Lys-; this fragment therefore appears to be essential for the activity of the analogues and is in fact also present in octreotide and lanreotide.

Recently, the hypothesis has been advanced that less-selective analogues, i.e. capable of interacting also with the other receptor subtypes, can offer an advantage from the standpoint of therapeutic use [Nature Rev. Drug Discovery 2, 999 (2003)].

In the patent application WO2002010192, a cyclopeptide is described which has a strong affinity for the receptor SSTR5, a lower affinity for SSTR2 and SSTR3 and a nearly zero affinity for SSTR4. For SSTR1, an affinity is described about 60 times less than that for SSTR5.

The same inventors of WO2002010192, in a subsequent publication [Nature Rev. Drug Discovery 2, 999 (2003)], sustain the importance of the receptors SSTR1, 2 and 5 for the antisecretory activity of somatostatin, but report, for the same cyclopeptide described in the aforesaid patent application, an affinity for SSTR1 of about 300 less than that for SSTR5.

It is clear that, in this case, a possible therapeutic activity mediated by the interaction with the receptor SSTR1 can only be achieved in the presence of a considerable overdosage with respect to the actions mediated by the interaction with SSTR5.

Therefore, while the possible therapeutic role of agonists for the receptor SSTR4 is not clear, there is clearly the need, and the possible use, for new somatostatin analogues with an affinity level comparable for all of the other four receptors.

In particular, the potential therapeutic advantages of agonists capable of interacting with SSTR1 are reported in the literature: M. C. Zatelli and colleagues have studied, in vitro, the effect of agonists for SSTR1 on human pituitary adenomas, both secreting [J Clin End&Met 88, 2797 (2003)] and clinically non-functional [J Clin End&Met 89, 5181 (2004)]; in both cases the stimulus of SSTR1 receptors lead to a reduction of the secretory activity and cell vitality. On the other hand, the potential therapeutic advantage that can derive from the use of pluripotent analogues of somatostatin (capable of interacting with the receptors SSTR 1, 2, 3 and 5) was also shown by J. van der Hoek and colleagues in a recent review [Curr. Pharm. Design 11, 1573 (2005)]; it was in fact shown how different tumours, both pituitary and gastroenteropancreatic (GEP), express, on the cell surface, variable but significant percentages of all four receptors, while the receptor SSTR4 is much less present.

The application WO2005014624 describes the preparation of cyclic analogues of somatostatin and the intermediates used in their preparation. These hexacyclic analogues have the tryptophan residue in position 3.

The application WO2006066868 describes pharmaceutical compositions for the parenteral administration of several salts of somatostatin analogues, which form a deposit gel after the injection in contact with the body fluids. By somatostatin analogues, it is intended the linear or cyclic peptides derived from somatostatin, which comprise a sequence of amino acids comprising tryptophan.

In *Regulatory Peptides*, 1 (1980) 97-113, the importance of the indole NH group is sustained for the somatostatin activity: the substitution of $Trp^8$ with naphthylalanine in fact causes the loss of activity.

The binding data is not reported in the article, while the inhibition activity of the in vivo gastric secretion is evaluated. The results indicate that, for the gastric activity, the substitution of $Trp^8$ with halogen, methylated or methoxylated analogues (table II) has little influence on the biological potency, potency which is instead nearly cancelled in the analogues containing pentamethyl-phenylalanine (Pmp) or naphthylalanine (table III), rather than tryptophan. The deriving halogen compounds of D-Trp instead seem to considerably improve the inhibition activity of the GH secretion (table V). Merck S&D researchers (see Veber D. F. in *Proceedings of the 12th Am. Pep. Symp.*; Smith, J. A. & Rivier J. E. editors, ESCOM 1992, pp 3-14) report that, in cyclic hexapeptides, the substitution of the tryptophan with other aromatic amino acids leads to a considerable loss of in vitro activity in the inhibition of the GH secretion.

In *J Med Chem* (2005) 48, 507, selective analogues for SSTR1 are described along with their possible therapeutic role of agonists. The structures analysed here also have tryptophan.

The article describes two series of analogues derived from two cyclopeptides: one containing D-Trp and the other D-Nal; all the analogues, like the parents, only have affinity for SSTR1; the series with D-Nal is about 10 times less powerful than that with D-Trp. One particular detail of these peptides, which are inactive on all other receptor subtypes, is the substitution of the lysine with p-amine-phenylalanine.

From that set forth above, it is therefore evident that a pluripotent agonist of somatostatin, i.e. capable of stimulating SST1, SSTR2, SSTR3 and SSTR5, will increase the possibility of positive responses in patients affected by neuroendocrine tumours with respect to agonists whose activator function is restricted to a lower number of sub-receptors of the somatostatin.

DESCRIPTION OF THE INVENTION

The applicant has surprisingly found that the tryptophan residue, present in many known analogues, can be usefully substituted with other suitable aromatic residues, maintaining the affinity for most of the somatostatin receptors.

In particular, it was found that, by using amino acids whose aromatic group is sufficiently rich with electrons (being, for example, substituted with electron-donor groups) in substitution of the tryptophan residue, peptides are obtained which show a good affinity for the SSTR1 receptor, at concentration values similar to those necessary for the bond to the SSTR2, SSTR3 and SSTR5 receptors.

Forming the object of the present invention are therefore somatostatin analogue cyclohexapeptides, having formula (I), where by somatostatin analogue cyclohexapeptides it is intended peptides with six alpha-amino acid residues, in which a direct peptide bond is present between the alpha-carboxyl group of the sixth residue and the alpha-amine group of the first residue, with bond affinity at nanomolar concentrations, for at least one of the known somatostatin receptors:

Formula (I)

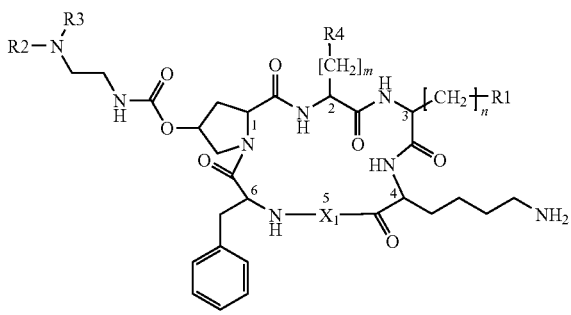

where:

m=0, 1 or 2 and n=1, 2 or 3; preferably m is equal to 1 and n is equal to 1 or 2; still more preferably n is equal to 1.

R1 represents an aromatic group, excluding indole, which is preferably phenyl, naphthyl, benzhydryl, fluorenyl, styrenyl, anthranyl or biphenyl, optionally substituted in one or more positions. The preferred substitution groups are those electron-donors such as alkyl, alkyloxyl, hydroxyl, alkylamine, acylamine, sulphide or alkylsulphide.

The group R1 is preferably naphthalene group, substituted with or more methyloxy groups, preferably with two methyloxy groups; in a still more preferred aspect of the invention, R1 is 3,8-dimethoxy-naphthalene-2-yl.

R4 represents an aromatic group, optionally substituted. The R4 group is preferably a phenyl group, possibly substituted with a hydroxyl group, $C_1$-$C_4$ alkoxyl, $C_1$-$C_4$ alkyl, halogen or nitro.

R2 and R3 are, independently, H or a $C_1$-$C_4$ alkyl group, or, together, they represent a $C_4$-$C_5$ alkylene chain, bonded to the nitrogen atom to form a cyclic structure.

Alternatively, R3 can be a cation or metal chelating group, directly joined to the amine group or joined through a spacer.

The possible spacer can be one of those already known in the art, for example those described in GB-A-2,225,579 or in WO9701579, incorporated here by reference; they can, for example be a group of formula —Z—R5-CO—, where R5 is $C_{1-11}$ alkylene, $C_{1-11}$ alkenylene or —CH(R6)-, where R6 is the side chain of an alpha amino acid, and Z is a function capable of forming a covalent bond with the chelating group; Z can for example be a functional group capable of forming an ether, ester or amidic bond with another functional group of the chelating group (for example hydroxyl, carboxyl or amine) Z preferably is an oxygen atom, a sulphur atom, a carbonyl radical (or CO) or an amino radical (or NH).

The group Z is still more preferably an amino radical and the group of formula —Z—R5-CO— will be a bivalent residue deriving from a carboxylic-amino acid, such as, for example, beta-Alanine (or —NH—$(CH_2)_2$—CO—), 6-amino hexanoic acid (or —NH—$(CH_2)_5$—CO—) or others.

The chelating group is a physiologically acceptable group, capable of complexing ions or other detectable or useful elements for anti-tumour radiotherapy and preferably has a hydrophilic character.

The chelating groups and the ions and other complexing elements can be usefully chosen from among those already known and described, for example, by Okarvi S. M. in Med. Res. Rev. 24 (3), 357 (2004), by Weiner R. E. and Thakur M. L. BioDrugs 19(3), 145 (2005) or in WO2002010192, incorporated here by reference.

The chelating group can be in free form, salified or complexed with ions or other elements, detectable by radioactivity (radionuclides) or with other means, or usable for radiotherapeutic aims.

Preferably, the chelating group will be derived from 1,4,7,10-tetraazacyclododecane-N,N',N'',N'''-tetraacetic acid (DOTA) or diethylenetriaminepentaacetic acid (DTPA) and the ion will be a paramagnetic ion ($Gd^{3+}$, $Fe^{3+}$, or others), fluorescent ($Eu^{3+}$) or a radionuclide emitting $\alpha$, $\beta$ or $\gamma$ radiations (111In, 99mTc, 169Yb, 177Lu, 90Y, 213Bi or others).

X1 is an aminoacyl residue of formula (a), (b) or (c)

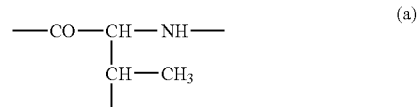

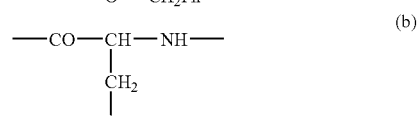

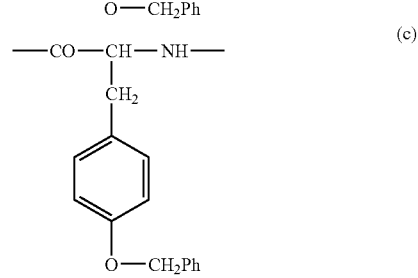

X1 is preferably an aminoacyl residue of formula (c).

The aminoacyl residues, present in the cyclohexapeptides of formula (I), can have configuration L or D; preferably the residues 1, 2, and 4-6 are L, and the residue 3 is preferably D.

The cyclohexapeptides of formula (I) can exist in free base form or as salts. The salts include addition salts with organic acids (for example acetates, lactates, benzoates, aspartates, pamoates, etc.), polymer acids (for example polymethacrylic acid, polystyrenesulfonic acid, etc.) or inorganic acids (for example hydrochlorides, sulphates, nitrates, etc.).

The compounds of the invention are, in vivo, much more resistant to the degradation mechanisms in comparison with the analogue cyclodisulphides of somatostatin (octreotide, lanreotide, etc.) and consequently have a longer action duration. In some cases, the stability and action duration are also improved with respect to other cyclopeptides, including those already known for being stable somatostatin agonists.

The present invention also includes the processes for the production of compounds of formula (I), from here on called compounds of the invention.

The compounds of the invention can be produced by using different synthetic methods, analogous to methods already known for other peptides.

a) A corresponding linear hexapeptide, partially protected, can be produced by means of solid phase synthesis, so as to leave both the N-terminal alpha-amino group and the C-terminal alpha-carboxylic group free; the two free groups will the be made to react, in solution, by means of appropriate condensing agents and the protections of the side chains will finally be removed, obtaining the desired cyclohexapeptide.

b) Alternatively, the solid phase synthesis can be conducted by anchoring the peptide to the resin by means of the lysine side chain; in this case, after having selectively removed the protections from the N-terminal and C-terminal groups, the cyclisation can still be conducted in solid phase and the compounds of the invention can be obtained with a single treatment of deprotection and separation from the resin.

c) In another alternative, the protected linear peptide can be prepared by means of synthesis in solution and then, after having selectively removed the protections from the N-terminal and C-terminal groups, one can proceed as described in a). The linear peptide to be cyclised can be chosen from among six peptides hypothetically obtainable by means of the opening of any one of the six peptide bonds present in the compounds of the invention. The choice will be guided by considerations of synthetic suitability, known to peptide synthesis experts, but do not minimally influence the nature of the final product, which will in any case be identical whatever the chosen sequence of the linear peptide; preferably, peptides are chosen in which the C-terminal amino acid is lysine.

Many of the amino acid derivatives, necessary for the synthesis of the peptides, are known and commercially available.

The hydroxyproline derivates can be prepared as described in WO9701579, incorporated here by reference, or with other similar procedures; alternatively, the partially protected linear peptides can contain a non-modified hydroxyproline residue, and the introduction of the side chain can be carried out directly on the linear peptides, before the deprotection, or after the cyclisation, before the final deprotection.

For the chelating derivatives of the compounds of the invention, the protector group of the chain bonded to the hydroxyproline can be appropriately chosen such that it is possible to selectively remove it, leaving the protection of the lysine side chain unaltered; in this manner, it will be possible to bind the chelating group to the free amino group, directly or by means of a spacer, before the final deprotection.

Some amino acids used in position 3 of the general formula (I), like their derivatives, are new and form a further aspect of the present invention. In particular, we refer to the amino acids:
3-(3,8-dimethoxy-naphthalene-2-yl)-alanine,
3-(1,4-dimethoxy-naphthalene-2-yl)-alanine and
2,5-dimethoxy-homophenylalanine
and to their totally or partially protected derivatives, corresponding to the formulas (e), (f) and (g):

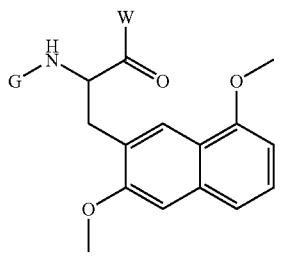

(e)

3-(3,8-dimethoxy-naphthalene-2-yl)-alanine and derivatives

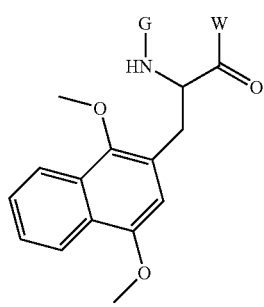

(f)

3-(1,4-dimethoxy-naphthtalene-2-yl)-alanine and derivatives

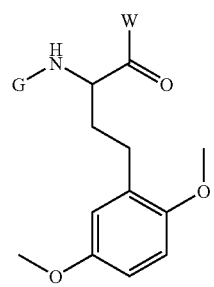

(g)

2,5-dimethoxy-homophenylalanina and derivatives

In formulas (e), (g) and (f), G can be a hydrogen atom or a protective group chosen from among those known to those skilled in the art, such as fluorene-9-yl-methyloxy-carbonyl, tert-Butyloxy-carbonyl or benzyloxy-carbonyl; W can be a hydroxyl group or a protective group chosen from among those known by those skilled in the art, for example methyloxy, tert-butyloxy or benzyloxy. By partially protected derivatives, it is intended those derivatives where only one, from among G and W, represents a protective group.

These can be prepared by adapting methods already known in literature (see for example [J Org Chem 55, 2913 (1990)], [Org. Lett. 2, 1089 (2000) and [Synthesis (1983), 38]); for example, starting from the aldehyde corresponding to the desired side chain, the method described in diagram 1 can be used.

DIAGRAM 1

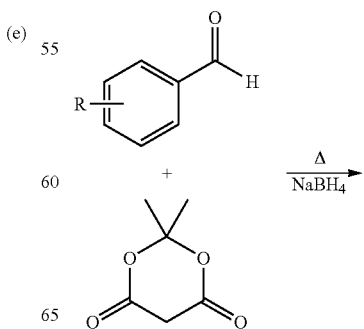

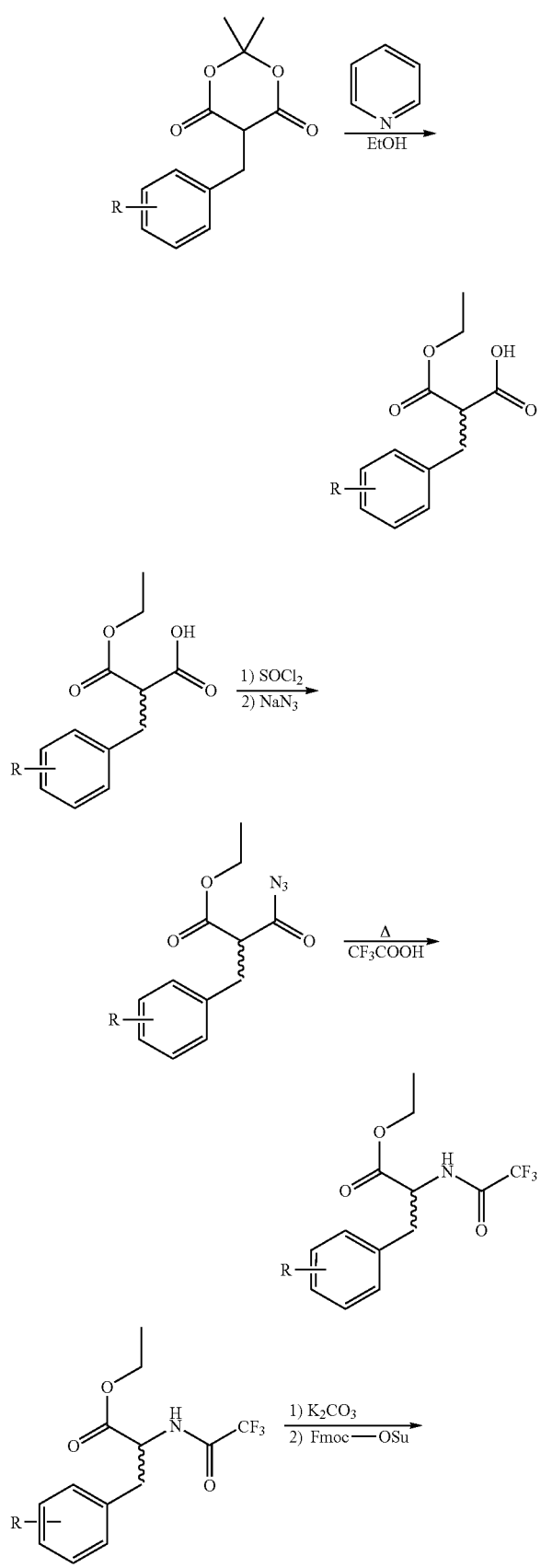

The aforesaid derivatives can be prepared as racemic enantiomer mixtures (D/L) or, by means of stereoselective synthesis or chiral resolution methods, they can be obtained as single enantiomers D or L.

Among the chiral resolution methods, enzymatic deracemisation methods can be used (such as, for example, that described in US2001021519, incorporated here by reference), in which the stereoselectivity of the enzyme (for example L or D amino acid-oxidase) allows inducing the racemisation of only one of the two enantiomers, after which repeated treatment cycles permit attaining high enantiomer purity.

Also object of the present invention are the pharmaceutical formulations which contain the compounds of the invention.

The compounds of the invention can be administered in free form or in the form of pharmaceutically acceptable salts or as complexes. Such salts and complexes can be prepared in a conventional manner and show the same order of activity as the free compounds. The present invention also provides pharmaceutical compounds comprising the compounds of formula (I) in free base form or in pharmaceutically acceptable salt form, together with one or more pharmaceutically acceptable excipients or diluents. Such compositions can be formulated in a conventional manner. The compounds of the invention also can be administered in modified release form, for example as implants, microcapsules, microspheres or nanospheres comprising, for example, biodegradable polymers or copolymers, in liposome formulation form, or in autogel form, for example solid or semisolid compositions capable of forming a gel after interaction with the fluids of the patient body.

The compounds of the invention or their pharmaceutically acceptable salts or complexes can be administered by means of any conventional pathway, for example parenterally, in the form of an injectable solution or suspension (also including the above-indicated modified release forms), orally, using a conventional absorption promoter, nasally or as suppositories or topically, for example in the form of an ophthalmic liquid, gel, preparation as unguent or as suspension, for example liposome suspension, as microsphere or nanosphere formulation, for example for subconjunctival or intra or periocular instillation or injection.

According to a further aspect of the invention, a pharmaceutical composition is also provided comprising a conjugate or a complex of compounds of the invention together with pharmaceutically acceptable excipients or diluents. Such compositions can be produced in a conventional manner and can be presented, for example for the diagnostic imaging, as a kit comprising two separate doses, one being the radionuclide and the other the conjugate of the compounds of the invention, with instructions for their mixing. For the radiotherapy, the conjugate of the compounds of the invention in complexed form can preferably be in hot liquid formulation form.

The following examples intend to illustrate the objects of the present invention and must not in any manner be considered limiting of the same.

In the examples, the following abbreviations will be used:
1,4MNal 3-(1,4-dimethoxy-Naphthalene-2-yl)-Alanine
2,5MhPhe 2,5-dimethoxy-homoPhenylalanine
3,8MNal 3-(3,8-dimethoxy-Naphthalene-2-yl)-Alanine
ACN Acetonitrile
Bn Benzyl
Boc tert-Butyloxy-carbonyl
DIPEA Diisopropylethylamine
DMF N,N-dimethylformamide
DPPA Diphenylphosphorylazide
DSC N,N-Disuccinimidylcarbonate
Fmoc Fluorene-9-yl-methyloxy-carbonyl
Fmoc-OSu Fluorene-9-yl-methyl, N-succinimidyl carbonate
HATU O-(7-Azabenzotriazole-1-yl)-N,N,N',N'-tetramethyluronium hexafluorophosphate
hPhe homoPhenylalanine; 2-amino-4-phenyl-butyric acid
Hyp 4,Hydroxy-proline
Nal 3-(Naphthalene-2-yl)-Alanine; 2-amino-3-napthalene-2-yl-propionic acid
NMM N-methyl Morpholine
Pd/C Metal palladium on carbon
Phg Phenylglycine; 2-amino-2-phenyl-acetic acid
PVDF Polyvinylidenefluoride
Sty Styryl-Alanine; 2-amino-5-phenyl-pent-4-enoic acid
Tfa Trifluoroacetyl
THF Tetrahydrofurane
-Trt(Cl)-DVB Resin, (2-chloro)Trityl-Divinylbenzene
Z Benzyloxy-carbonyl Except where otherwise indicated, the amino acids are in L configuration; with (D/L) the racemic amino acids are indicated, while with (D,L) the single enantiomers of undefined chirality are indicated.

General Purification Method

If not otherwise indicated, all of the final purifications were carried out by means of a Waters preparation HPLC/MS system with Waters Symmetry C18 5 mm 19×50 mm columns, equipped with Waters ZQ mass spectrometer.

Operating Conditions:

ES+ centroid ionisation, 15 min scanning time, 120-1000 m/z scanning, 15V cone voltage, 120° C. source temperature, 250° C. solvation temperature.

HPLC Eluents:

A=$H_2O$, B=ACN, C=1% $CF_3COOH$ in $H_2O$

An aliquot of the raw product to be purified was dissolved in MeOH and diluted with an ACN/$H_2O$ (1:1; v/v) mixture. The solution, filtered on 0.45 mm PVDF membrane, was injected in the previously described preparation system. For every run, the fractions corresponding to the peak associated with the expected molecular ion ([M+H]$^+$) were collected, combined and concentrated to dryness. If additional peaks were presented associated with the same molecular ion (isomers), these were collected separately.

Preparation of the Intermediates

Example 1

Fmoc-(D/L) 3-(3,8-dimethoxy-Naphthalene-2-yl)-Alanine a) 3,8-dimethoxy-2-naphthaldeide (1 eq), 2,2-dimethyl-1,3-dioxane-4,6-dione (1.35 eq) and piperidine (0.12 eq) are dissolved in $CHCl_3$ and the solution is heated and refluxed for 2.5 hours. After aqueous washings, the product is recovered by evaporation of the solvent and redissolved in a mixture of THF and methanol, and $NaBH_4$ (5.4 eq) is added to the solution. After about 10 minutes, water is added and the mixture is acidified to pH=3. By partially evaporating, a solid is separated which is recovered and redissolved in ethanol, pyridine is added and the mixture is reflux heated until the initial product has completely disappeared (TLC control).

b) After having evaporated the ethanol, the product (monoethyl ester of 2-(3,8-Dimethoxy-naphthalene-2-yl-methyl)-malonic acid) is dissolved in chloroform and washed with acidic water. Thionyl chloride (1.3 eq) is added to the dried solution, and the mixture is reflux heated for about an hour. After repeated evaporations of the chloroform, the residue is dissolved in dichloromethane and the solution is cooled in an ice bath. Tetrabutylammonium bromide (catalytic) is added and $NaN_3$ (1.2 eq) dissolved in water, and after two hours at 0° C., the organic phase is recovered, which is washed with water and dried with anhydrous $Na_2SO_4$; the solution is left at room temperature, in the presence of anhydrous $Na_2SO_4$, for an entire night. Trifluoroacetic acid (1.5 eq) is added to the filtered solution, and the mixture is reflux heated for about 6 hours. After having washed with 5% $NaHCO_3$, the solvent is evaporated and the oil obtained is purified on a silica gel column.

c) The obtained product (Tfa-(D/L)3,8MNal-OEt) is dissolved in a mixture of THF, methanol and water, containing $K_2CO_3$ (2 eq) and reflux heated for one night. The solution is partially evaporated and Fmoc-OSu (1 eq) dissolved in THF is added. Upon completed reaction (TLC control), the THF is evaporated and the product recovered by extracting the aqueous solution with ethyl acetate. With the addition of n-hexane, one obtains the precipitation of the product (Fmoc-(D/L)3,8MNal-OH) which is filtered and dried (HPLC purity: 98.5%; m/z=498 amu ([M+H]+)).

Example 2

Fmoc-[4-(2-aminoethyl)carbamoyl]Proline a) Z-Hyp-OBn and DSC (1 equivalent) are dissolved in acetonitrile and treated with triethylamine (1.2 eq). After a night at room temperature, N-Boc-diamineethane (1.2 eq) is added and the mixture is left to react for 3.5 hours. After evaporation of the solvent, the residue recovered with ethyl acetate is washed, in order, with 2.5% $KHSO_4$, $NaHCO_3$ and NaCl. The organic solution, dried with anhydrous $Na_2SO_4$, is evaporated to dryness, recovering the product.

b) The product is dissolved in methanol and the protector groups (Z and benzyl ester) are removed by means of catalytic hydrogenation in the presence of 10% Pd/C. After filtration of the catalyst, the amino acid is recovered by evaporating the solvent, and is dissolved in a mixture of water and THF containing $K_2CO_3$ (1 eq), and after having cooled to 0° C. Fmoc-OSu (2 eq) dissolved in THF is added. Upon completed reaction (TLC control), the THF is evaporated and the product recovered by extracting the aqueous solution with ethyl acetate. With the addition of n-hexane, one obtains the precipitation of the product, which is filtered and dried (HPLC purity: 99.9%; m/z=540 amu ([M+H]$^+$))

Example 3

Fmoc-(D/L) 2,5-dimethoxy-homophenylalanine a) To a suspension of 2,2-dimethyl-1,3-dioxane-4,6-dione (1.3 eq) in DMF (50 mL), cooled in an ice bath, $NaCNBH_3$ (1.8 eq) and 2.5-dimethoxyphenylacetaldeide (1.1 eq) are added. The reaction mixture is stirred at RT for 5 h. By adding $H_2O$, a solid is separated which is filtered, purified by crystallisation from isopropanol and finally dissolved in EtOH and reflux treated with pyridine for six hours.

b) Operating as described in point b) of example 1, from the obtained product (mono-ethyl ester of 2-(2,5-Dimethoxy-phenyl-ethyl)-malonic acid), the partially protected amino acid Fmoc-(D/L)2,5 MhPhe-OH is prepared (HPLC purity: 96%; m/z=462 amu ([M+H]$^+$)).

Example 4

Fmoc-(D/L) 3-(1,4-dimethoxy-Naphthalene-2-yl)-Alanine

Starting from 1,4-dimethoxy-2-naphthaldeide and operating as described in example 1, the protected amino acid Fmoc-(D/L)1,4MNal-OH is obtained. (HPLC purity: 96.9%; m/z([M+H]+)=498 amu).

Preparation of the Cyclopeptides

The purity of the peptides described in the examples was analysed by means of HPLC reverse-phase chromatography (Agilent 1100 chromatograph), using the following method:
Eluents: A) 0.1% TFA in acetonitrile/water (5:95; v/v)
B) 0.1% TFA in acetonitrile
Eluent B gradient: from 20% to 80% in 30 min.
Flow: 1.0 ml/min.
Column: Jupiter 4μ (4×250 mm)

Example 5 cyclo[Tyr(Bn)-Phe-Pro(4-OCONH(CH$_2$)$_2$NH$_2$)-Phe-(D,L)3,8MNal-Lys]isomer B a) H-Tyr(Bn)-Phe-Pro(4-OCONH(CH$_2$)$_2$NHBoc)-Phe-(D/L)3,8MNal-Lys(Boc)-OH Starting from the resin Fmoc-Lys(Boc)-Trt(Cl)-DVB, various cycles of solid phase peptide synthesis are carried out, in order to obtain the desired hexapeptide; in the first cycle, one uses Fmoc-(D/L)3,8Mnal-OH (see ex. 1) and in the third cycle one uses Fmoc-Pro(4-OCONH(CH$_2$)$_2$NHBoc)-OH (see ex. 2); for every cycle, the Fmoc group is removed with 20% Piperidine in DMF and the subsequent amino acid, protected like Fmoc, is activated with HATU and made to react with the amino groups present on the resin.

At the end, the Fmoc group is removed with 20% Piperidine in DMF and the partially protected peptide is removed from the resin by means of a treatment with a mixture of acetic acid, trifluoroethanol and dichloromethane (in 1:2:7 proportion) for 30 minutes at room temperature. After having evaporated the solvent, the residue is divided between ethyl acetate and 5% NaHCO$_3$, the organic phase is recovered and evaporated, obtaining a solid residue.

b) cyclo[Tyr(Bn)-Phe-Pro(4-OCONH(CH$_2$)$_2$NH)-Phe-(D,L)3,8-MNal-Lys]

The peptide obtained in c) is dissolved in (1.6 mM) DMF and cooled to −10° C.; DIPEA (2 eq) and DPPA (1.3 eq) are added and the mixture is left at +4° C. for 60 hours. After having removed DMF, the residue is recovered with ethyl acetate and washed with 5% NAHCO$_3$. By evaporating the organic phase, one obtains a solid residue which is treated with TFA (95% in H2O) at 0° C. for 1 hour and then evaporated; different isomer species are present in the residue, which are separated by means of reverse-phase chromatography (column C18). The second isomer, in the order of elution from the HPLC column, (isomer B), is collected pure.

HPLC: RT 14.74 min.; 99.1% purity
MS: m/z=1133 amu ([M+H]$^+$) and 567 amu ([M+2H]$^{2+}$)

Example 6 cyclo[Tyr(Bn)-Phe-Pro(4-OCONH(CH$_2$)$_2$NH$_2$)-Phe-(D,L)2,5 MhPhe-Lys] isomer B a) H-Tyr(Bn)-Phe-Pro(4-OCONH(CH$_2$)$_2$NHBoc)-Phe-(D/L)2,5-MhPhe-Lys(Boc)-OH One operates as described in point a) of example 5, using Fmoc-(D/L)2,5MhPhe-OH (ex. 3) in the first cycle and Fmoc-Hyp-OH in the third cycle. Before the removal of the terminal Fmoc group, the resin is treated with p-nitrophenyl-chloroformate (5 eq) in the presence of NMM (5 eq); after three hours, the resin is washed with DCM and treated with N-Boc-diamineethane (5 eq) for another three hours, and then filtered and washed. One then proceeds as described in point a) of example 5.

b) cyclo[Tyr(Bn)-Phe-Pro(4-OCONH(CH$_2$)$_2$NH)-Phe-(D,L)2,5-MhPhe-Lys]

The peptide obtained in a) is treated as described in point b) of example 5. Also in this case, one obtains different isomers, which are separated by means of reverse-phase chromatography (column C18). The second isomer, in the order of elution from the HPLC column, (isomer B), is collected pure.

HPLC: RT 13.82 min.; purity 99.0%
MS: m/z=549 amu ([M+211]$^{2+}$)

Example 7 cyclo[Tyr(Bn)-Phe-Pro (4-OCONH(CH$_2$)$_2$NHCH$_3$)-Phe-(D,L)3,8MNal-Lys] isomer B One operates as described in example 6, using Fmoc-(D/L)3,8MNal-OH (ex. 1) in the first cycle and Boc-N(CH$_3$)—(CH$_2$)$_2$—NH$_2$) to modify the side chain of hydroxyproline. Different isomers are obtained, which are separated by means of reverse-phase chromatography (colonna C18). The second isomer, in the order of elution from the HPLC column, (isomer B), is collected pure.

HPLC: RT 15.07 min.; purity 94.5%
MS: m/z=1147 amu ([M+H]$^+$) and 574 amu ([M+2H]$^{2+}$ Example 8 cyclo[Tyr(Bn)-Phe-Pro(4-OCONH(CH$_2$)$_2$NH$_2$)-Phe-(D,L)1,4-MNal-Lys] isomer A One operates as described in example 6, using Fmoc-(D/L)1,4MNal-OH (ex. 4) in the first cycle. Different isomers are obtained, which are separated by means of reverse-phase chromatography (column C18). The isomer with lower retention time (isomer A) corresponds to the product of the title.

HPLC: RT 13.71 min.; purity 80.6%
MS: m/z=1133 amu ([M+H]$^+$) and 567 amu ([M+2H]$^{2+}$))

Example 9 cyclo[Tyr(Bn)-Phe-Pro(4-OCONH(CH$_2$)$_2$NH$_2$)-Phe-(D,L)1,4-MNal-Lys] isomer B From the preparation described in the previous example, the isomer B is also collected pure, the second in the order of elution from the HPLC column. HPLC: RT 14.71 min.; purity 97.7%
MS: m/z=1133 amu ([M+H]$^+$) and 567 amu ([M+2H]$^{2+}$)

Example 10 cyclo[Tyr(Bn)-Phe-Pro (4-OCONH(CH$_2$)$_2$NH$_2$)-Phe-(D)Nal-Lys]

The compound is synthesised following the procedure described in example 6, using Fmoc-(D)Nal-OH in the cycle.
HPLC: RT 14.14 min.; purity 99.5%
MS: m/z=1073 amu ([M+H]$^+$) and 537 amu ([M+2H]$^{2+}$)

Example 11 cyclo[Tyr(Bn)-Phe-Pro(4-OCONH(CH$_2$)$_2$NH$_2$)-Phe-(D)hPhe-Lys]

The compound is synthesised by following the procedure described in example 6, using Fmoc-(D)hPhe-OH in the first cycle.
HPLC: RT 13.81 min.; purity 94.5%
MS: m/z=1037 amu ([M+H]$^+$) and 519 amu ([M+2H]$^{2+}$)

Example 12 cyclo[Tyr(Bn)-Phe-Pro (4-OCONH(CH$_2$)$_2$NHCH$_3$)-Phg-(D) Sty-Lys]

The compound is synthesised following the procedure described in example 7, using Fmoc-(D)Sty-OH in the first cycle and Fmoc-Phg-OH in the second cycle.
HPLC: RT 13.62 min.; purity 97.8%
MS: m/z=1049 amu ([M+H]$^+$) and 525 amu ([M+2H]$^{2+}$)

Example 13 cyclo[Tyr(Bn)-Phe-Pro(4-OCONH(CH$_2$)$_2$NH$_2$)-Phg-(D)hPhe-Lys]

The compound is synthesised following the procedure described in example 6, using Fmoc-(D)hPhe-OH in the first cycle and Fmoc-Phg-OH in the second cycle.
HPLC: RT 12.78 min.; purity 98.8%
MS: m/z=512 amu ([M+2H]$^{2+}$)

Example 14 cyclo[Tyr(Bn)-Phe-Pro(4-OCONH(CH$_2$)$_2$NH$_2$)-Tyr-(D,L)3,8MNal-Lys] isomer B

One operates as described in example 5, using Fmoc-Tyr(tBu)-OH in the second cycle.
HPLC: RT 13.13 min.; purity 95.4%
MS: m/z=1149 amu ([M+H]$^+$) and 575 amu ([M+2H]$^{2+}$)

Example 15 cyclo[Ser(Bn)-Phe-Pro(4-OCONH(CH$_2$)$_2$NH$_2$)-Phe-(D,L)3,8MNal-Lys] isomer B

One operates as described in example 5, using Fmoc-Ser(Bn)-OH in the fifth cycle.
HPLC: RT 12.26 min.; purity 98.2%
MS: m/z=1057 amu ([M+H]$^+$) and 529 amu ([M+2H]$^{2+}$)

Experimental Part

The compounds of the invention show important pharmacological properties, as indicated in several in vitro and in vivo tests.

In particular, the compounds of the invention bond, with good affinity, to at least one of the subtypes of the receptors of the somatostatin.

Binding Assays

The binding assays were carried out, as is explained below, by using preparations of recombinant human receptors, hSSTR1, hSSTR2, hSSTR3 and hSSTR5, obtained from cell membranes (for example CHO) transfected according to standard methods.

The membranes are incubated in duplicate for 60 min. at 25° C. with 3-[125I]iodotyrosyl11Somatostatin-14 (Amersham, IM161, 2000 Ci/mmol) as radioligand and with increasing concentrations of the compound under examination, in 25 mM Hepes (pH 7.4) buffer, containing 5 mM MgCl$_2$, 1 mM CaCl$_2$, 10 µg/ml of Saponin, 0.5% BSA. The incubation is terminated by means of filtration with a Filtermate Harvester (Perkin Elmer) through GF/B filters, which are then washed 6 times with buffer (25 mM Hepes pH 7.4, 5 mM MgCl$_2$, 1 mM CaCl$_2$). The radioactivity of the filters is measured in a TopCount™ or MicroBeta™ reader for 1 min/well after having added the Microscint 20 liquid scintillation (Packard) and incubated for 15 min. in an orbital stirrer. The results are expressed as specific binding percentage of the radio-marked ligand, in the presence of increasing concentrations of the compound under examination. The IC$_{50}$ values were calculated by using the "GraphPad Prism" software (IC50=concentration of compound necessary for obtaining half of the maximum inhibition, in the competitive binding test described above).

The IC50 values of the compounds of the invention are situated in the nMolar concentration field, preferably comprised between 0.1 and 50 nM.

|  | IC50 (nM) | | | |
| --- | --- | --- | --- | --- |
| Compound | hSSTR1 | hSSTR2 | hSSTR3 | hSSTR5 |
| Example 5 | 10.8 | 9.3 | 0.31 | 0.42 |
| Example 6 | 10.0 | 25.8 | 0.52 | 0.64 |
| Example 7 | 5.8 | 9.2 | 1.33 | 0.97 |
| Example 8 | 19.1 | 26.6 | 2.92 | 9.78 |
| Example 9 | 32.4 | 9.9 | 2.34 | 1.90 |
| Example 10 | 113.8 | 1.7 | 1.22 | 0.52 |
| Example 11 | 26.9 | 21.3 | 1.34 | 1.18 |
| Example 12 | 39.3 | 3.3 | 4.03 | 4.86 |
| Example 13 | 84.7 | 31.9 | 3.02 | 0.54 |
| Example 14 | 21.7 | 1.8 | 0.35 | 0.36 |
| Example 15 | 1.0 | 7.0 | 1.80 | 1.62 |

Assay for the Inhibition of the Growth Hormone Release on Rat Pituitary Cells

The compounds of the invention also show an inhibition activity of the growth hormone release (GH), as shown from tests carried out in vitro on rat pituitary cells. The hypophysial glands drawn from adult male rats (CD1-SD, 175-200 g) are cut into little pieces and incubated with collagenase (1 mg/ml) in Hank's buffer containing 1% BSA, 20 mM Hepes, antibiotics, for 20 min. at 37° C. The dispersed cells, after having been washed several times with buffer, are distributed, with 20000 cells/well, into 48 well plates and are maintained in culture for 6-7 days (DMEM containing 5% foetal bovine serum, 5% horse serum, 1% non-essential amino acids). On the day of the experiment, the cells are washed with Hank's buffer and are then incubated at 37° C. for 1 h in the presence of Hank's buffer added with 0.1% BSA and 20 mM HEPES. The buffer is then substituted with fresh buffer, still in the presence of 0.1% BSA and 20 mM HEPES. The cells are then incubated for 3 h at 37° C. in a $CO_2$ incubator with various concentrations of the products under examination and with 3×10-9 M GHRH. The GH released in the medium is measured by using the Kit ELISA Rat Growth Hormone Biotrack Enzymeimmunoassay (Amersham RPN2561) or the Kit Mouse/Rat GH ELISA (DSL-10-72100) according to supplier indications. The compounds of the invention inhibit the release of GH at concentrations in the range of 10-11 to 10-6 M; the compound of example 5 has an IC50 value of 1.3 nM.

Assay for the Inhibition of the Growth Hormone Release on Human, GH-Secreting Hypophysial Adenoma Cells The compounds of the invention also show an inhibition activity of the GH release from human, GH-secreting hypophysial adenoma cells, as indicated from in vitro tests on clinical tumour reports. The test is executed by using human tumour biopsies; the GH produced from the non-stimulated cells, in the presence of variable quantities of the compound under examination, is measured by using the kit ELISA hGH-EASIA (biosource KAP1081) according to the indications of the supplier. In the tumours sensitive to the action of Somatostatin and analogues, the compounds of the invention halve the GH production at concentrations in the range of 10-10 to 10-6 M; preferably at the concentration of 10 nM.

Assay for the In Vivo Inhibition of the GH Production, Stimulated by Barbiturates The compounds of the invention inhibit, in vivo, the release of GH stimulated by the administration of Nembutal. The compounds are administrated subcutaneously, at different doses, in male rats (CD, Harlan Italy). Blood samples are collected, at different times, one hour after the animals were anesthetised by means of intraperitoneal administration of Nembutal (60 mg/kg); the hormone levels are measured by means of the ELISA test. In the animals treated with the compounds of the invention, at doses from 5 to 250 µg/kg, there is a decrease of the produced GH levels. The compound of example 1, at the dose of 5 µg/kg, reduces by 55% the release of GH measured six hours after the administration; at the dose of 125 µg/kg the reduction of GH is still measurable 24 hours after the administration.

Assay for the Pharmacokinetic Profile

The compounds of the invention also show, in rats, a very favourable pharmacokinetic profile. The pharmacokinetic profile was measured by administering the compounds to male rates, subcutaneously, at the dose of 1 mg/kg (CD, Sprague Dawley; 200-250 g). Blood samples were collected, at different times, up to 72 hours after the administration. The concentrations of the compound under examination were measured in the separated plasma samples, by means of an LC-MS/MS analysis method and the values were processed according to a non-compartmental model using the software "Kinetica". In the following table, the main pharmacokinetic parameters obtained with the compound of example 1 are reported, compared with those obtained with PASIREOTIDE, another stable analogue of somatostatin, currently in clinical development phase (PASIREOTIDE was prepared by following the process described in WO2002010192).

|  |  | Example 5 | PASIREOTIDE |
|---|---|---|---|
| Dose | (mg/kg) | 1 | 1 |
| Cmax | (ng/mL) | 224.02 | 667.88 |
| tmax | (h) | 4 | 2 |
| t½ | (h) | 31.3 | 24.4 |
| AUC0-t | (ng/mL * h) | 2728.50 | 2781.40 |
| AUCtot | (ng/mL * h) | 2883.06 | 2795.85 |
| MRT | (h) | 18.96 | 4.87 |

The compound of example 5 is better than PASIREOTIDE both in terms of half-life and for the mean residence time (MRT); in the case of OCTREOTIDE, the t½ value is about 2 hours.

The compounds of the invention are consequently useful for the prevention or treatment of disorders with an origin that comprises or is associated with an excess of GH secretion and/or an excess of IGF-1, such as in the treatment of acromegaly, in the treatment of type I or type II diabetes mellitus, especially in their complications, such as for example angiopathy, proliferative diabetic retinopathy, diabetic macular edema, nephropathy and hyperglycemic phenomenon upon waking and other metabolic disorders connected with the release of insulin or glucagon, such as for example morbid obesity or hypothalamic obesity or hyperinsulenimic obesity. The compounds of the invention are useful also in the treatment of enterocutaneous and pancreatic cutaneous fistulas, irritable intestine syndrome, inflammatory diseases, such as for example Grave's disease, irritable intestine disease, psoriasis or rheumatoid arthritis, polycystic kidney disease, rapid gastric emptying disease, aqueous diarrhoea syndrome, diarrhoea connected with AIDS, diarrhoea induced by chemotherapy, acute or chronic pancreatitis, gastrointestinal hormone-secreting tumours (for example GEO tumours, such as vipomas, gluconomas, insulinomas, carcinoids and the like), malignant lymphocytes, such as lymphomas or leukaemias, hepatocellular carcinomas like gastrointestinal bleeding, like esophageal varicose bleeding.

The compounds of the invention are also useful in the treatment of tumours positive for the somatostatin receptors, such as for example the tumours which bear the receptors SSTR1, SSTR2, SSTR3 and/or SSTR5, as indicated in the proliferative tests with various cancer cell lines which express the receptors for somatostatin.

For all of the abovementioned indications, the required dosage will naturally vary in relation to, for example, the patient, the administration mode and the severity of the conditions which must be treated. Generally, however, one obtains satisfying results with administrations from 1 µg up to 0.7 mg/kg/day of the compounds of the invention. A recommended daily dosage for patients is on the order of about 2 µg up to 50 mg, preferably from about 0.01 to about 40 mg, for example from about 0.001 to about 3 mg s.c. of the compound conveniently administered in divided doses, up to 3 times per day, in single dosage forms containing, for example, from about 0.5 µg to about 25 mg, for example from about 2 µg to about 20 mg, for example from about 2 µg to about 1.5 mg of the invention compounds. The conjugates of the compounds of the invention or their pharmaceutically acceptable salts are useful both as agents for the diagnostic imaging, for example for the display of tissues and cells positive for the somatostatin receptors, such as the tumours and metastases positive for the somatostatin receptors, and for the inflammatory or autoimmune disorders which show somatostatin receptors, tuberculosis or the rejection of organs after transplant, when complexed with a detectable element, such as for example the γ nuclides or emitting positrons, a fluorescent metal ion or a paramagnetic ion, such as for example $^{111}$In, $^{161}$Tb, $^{177}$Lu, $^{68}$Ga, $Eu^{3+}$, $Gd^{3+}$, $Fe^{3+}$, $Mn^{2+}$ or $Cr^{2+}$, or as radio-drugs for the in vivo treatment of tumours and metastases positive for the somatostatin receptors, for rheumatoid arthritis, and severe inflammation conditions, when complexed with a α- or β-emitting nuclide with a cascade of Auger electrons, for example $^{90}$Y, $^{161}$Tb, $^{177}$Lu, $^{211}$At, $^{213}$Bi $^{201}$Tl.

The conjugates of the compounds of the invention in complexed form for use in the diagnostic imaging can be administered intravenously, for example in injectable solution or suspension form, preferably in single injection form. The radiotracers can preferably be made just before the patient administration.

In animals, a recommended dosage range can be from 0.01 to 1 μg/kg of conjugate of the compounds of the invention, complexed with 0.02-0.5 mCi of γ-emitting radionuclide. In the largest mammals, such as humans, a recommended dosage range can be from 1 to 100 μg/m$^2$ of conjugate of the compounds of the invention complexed for example with 1-100 mCi/m$^2$ of detectable element, such as $^{111}$In, $^{86}$Y or $^{177}$Lu.

The dosages used in the radiotherapeutic use practice of the present invention will of course depend on the particular conditions which must be treated, for example the known radiotoxicity for healthy organs which express the somatostatin receptors, the size of the tumour mass and the desired therapy. In general, the dose is calculated based on the pharmacokinetic data and distribution data of the radioactivity obtained from healthy organs and based on the uptake observed on the target. A β-emitting complex or a conjugate of the compounds of the invention can be repeatedly administered, for example for a period of 1-3 months.

In animals, a recommended dosage range can be from 20 to 100 μg/kg of conjugate of the compounds of the invention complexed with 15-70 mCi of an α- or β-emitting nuclide, or a nuclide with the Auger electron cascade, such as for example $^{90}$Y, $^{177}$Lu or $^{161}$Tb. In larger mammals, such as humans, a recommend dosage range can be from 1-100μ/m$^2$ of a complexed conjugated compound of the invention, for example from 1-100 mCi/m$^2$ of an α- or β-emitting nuclide or a nuclide with Auger electron cascade, for example $^{90}$Y, $^{177}$Lu or $^{161}$Tb.

The conjugates of the compounds of the invention in complexed form for use as radiotherapy agents can be administered through any conventional path, for example intravenously, for example in injectable solution form. They can be advantageously injected by infusion, for example with a 15-60 min infusion. Depending on the tumour site, it can be administered as close as possible to the tumour site, for example through a catheter. The present invention also provides a pharmaceutical composition comprising a conjugate of the compounds of the invention in free base form or as pharmaceutically acceptable salt or as complex with a detectable or radiotherapeutic agent, together with one or more pharmaceutically acceptable excipients or diluents.

The compounds of the invention or their conjugates in complexed form are useful for mapping or treating the tumours which express or accumulate the receptors, like the pituitary tumours, gastro-entero-pancreatic tumours, carcinoids, tumours of the central nervous system, breast tumours, prostate tumours (including advanced hormone-refractory prostate cancer), ovarian or colon tumours, small cell lung tumour, malignant intestinal occlusion, paragangliomas, kidney cancer, skin cancer, neuroblastomas, pheochromocytomas, medullary carcinoma of the thyroid, myelomas, lymphomas, Hodgkins lymphomas and non-Hodgkins lymphomas, bone tumours and their metastases, along with autoimmune or inflammatory disorders, for example rheumatoid arthritis, Grave's disease or other inflammatory diseases of the eye.

The compounds of the invention or their complexed conjugates can be administered as single active ingredient or they can be administered in combination, for example as adjuvants, with other active ingredients. For example, they can be used in combination with an immunosuppressive agent, for example an inhibitor of the calcineurin, like cyclosporine A or FK506; with a macrocyclic lactone having immunosuppressive properties, like rapamycin; with a monoclonal antibody with immunosuppressive properties or with an anti-inflammatory agent.

The compounds of the invention or their complexed conjugates can also be used in combination with an anti-proliferative agent, for example a chemotherapeutic active ingredient, like paclitaxel, gemcitabine, cisplatin, doxorubicin, 5-fluorouracyl or taxol, with a hormonal or antagonist agent, for example an anti-androgen or mitoxantrone (especially in the case of prostate cancer) or with an anti-estrogen, like letrozole (especially in the breast cancer cases), with a antimetabolite, with an alkaloid from a plant, with a biological response modifier, preferably an interferon or a lymphokine, with a protein tyrosine kinase inhibitor and/or with the serine/threonine kinases, with an enzyme inhibitor of histone-deacetylase or with an agent with other or unknown action mechanisms, such as for example anepothilone or epothilone derivatives, or with a macrocyclic lactone such as for example rapamycin, RAD or CCI779.

When the compounds of the invention or their conjugates in complexed form are administered in combination with another drug, the doses of the co-administered drugs will of course vary as a function of the conditions to treat and so on. The terms "co-administration" or "combined administration" or the like are used here to signify an administration of the therapeutic agents chosen for a single patient, and intend to include treatment regimes in which the agents are not necessarily administered by the same administration pathway or at the same time.

The particular combination of the invention will be selected depending on whether the disease or disorder must be prevented or treated; for example, a combination with immunosuppressive agent, for example for the prevention or treatment of chronic transplant rejection, a combination with an insulin secretagogue, with a promoter of the insulin secretion, with an insulin sensitiser or with a low insulin dose in the treatment of diabetes and in its complications, a combination with an anti-inflammatory agent for the prevention and treatment of inflammatory diseases or disorders, a combination with an agent with anti-angiogenic effect for the prevention or treatment for example of macular edema or degeneration or cancer, a combination with a chemotherapeutic agent for use in cancer.

The invention claimed is:

1. A cyclohexapeptide of formula (I):

Formula (I)

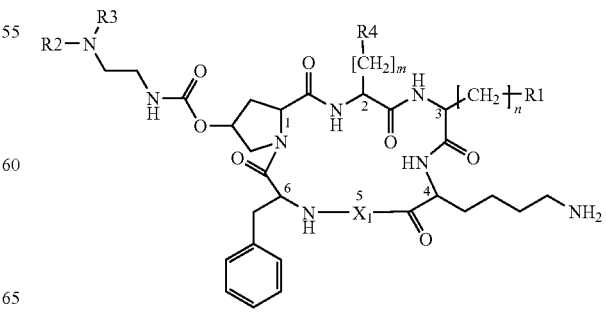

wherein m varies from 0 to 2; n varies from 1 to 3; R1 is 3,8-dimethoxy-naphthalene-2-yl, 1,4-dimethoxy-naphthalene-2-yl or 3-(naphthalene-2-yl); R4 is phenyl or 4-hydroxyphenyl; R2 and R3 are, independently, H or a $C_1$-$C_4$ alkyl group, or, together, they are a $C_4$-$C_5$ alkylene chain, bonded to the nitrogen atom in order to form a cyclic structure; or R3 is a cation or metal chelating group;

X1 is an aminoacyl residue of formula (a), (b) or (c)

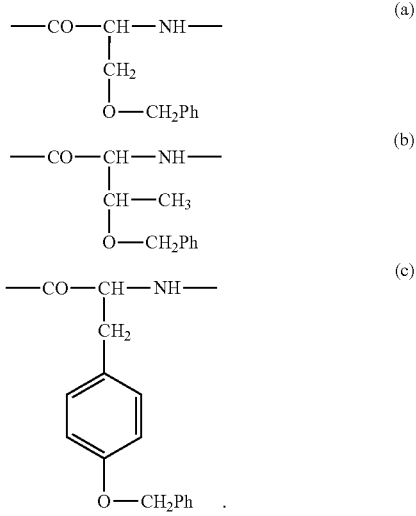

2. The cyclohexapeptide according to claim 1, wherein the ion or metal chelating group is directly joined to the amino group, or is joined through a spacer.

3. The cyclohexapeptide according to claim 2, wherein the spacer group is a group of formula —Z—R5-CO—, wherein R5 is $C_{1-11}$ alkylene, $C_{1-11}$ alkenylene or —CH(R6)-, wherein R6 is the side chain of an alpha amino acid, and Z is a functional group capable of forming an ether bond, ester bond or amidic bond with a functional group present on the chelating group.

4. The cyclohexapeptide according to claim 3, wherein Z is an oxygen atom, a sulphur atom, a carbonyl radical or an amino radical.

5. The cyclohexapeptide according to claim 1, wherein m is equal to 1 and n varies from 1 to 2.

6. The cyclohexapeptide according to claim 1, wherein the R3 group is a hydrophilic chelating agent.

7. The cyclohexapeptide according to claim 1, wherein the chelating group R3 is derived from 1,4,7,10-tetraazacyclododecane-N,N',N'',N'''-tetraacetic acid (DOTA) or diethylenetriaminepentaacetic acid (DTPA).

8. The cyclohexapeptide according to claim 1, wherein the chelating group R3 is a chelating group in free form, salified or complexed with cations or radioactive elements (radionuclides).

9. The cyclohexapeptide according to claim 8, wherein the chelating group R3 is complexed with a paramagnetic ion, such as $Gd^{3+}$, $Fe^{3+}$, or a fluorescent ion, such as $Eu^{3+}$ or a radionuclide emitting α, β or γ radiations, such as $^{111}In$, $^{99m}Tc$, $^{169}Yb$, $^{177}Lu$, $^{90}Y$ or $^{213}Bi$.

10. The cyclohexapeptide according to claim 1, wherein X1 is an aminoacyl residue of formula (c).

11. The cyclohexapeptide according to claim 1, wherein the aminoacyl residues of the cyclohexapeptide in formula (I), have configuration L or D.

12. The cyclohexapeptide according to claim 1, wherein one of the amino groups can optionally be in protected form, or in its salified or complexed form.

13. The cyclohexapeptide according to claim 12, mono- or disalified.

14. The cyclohexapeptide according to claim 13, wherein the salt is an addition salt with organic acids, polymer acids or inorganic acids.

15. The cyclohexapeptide according to claim 14, wherein the salts are chosen from among acetates, lactates, benzoates, aspartates, pamoates, polymethacrylates, polystyrenesulfonates, hydrochlorides, sulphates or nitrates.

16. The cyclohexapeptide according to claim 1, chosen from the group made up of
cyclo[Tyr(Bn)-Phe-[4-(2-aminoethyl)carbamoyl]Pro-Phe-(D,L)[3-(3,8-dimethoxy-naphthalene-2-yl)]Ala-Lys] isomer B,
cyclo[Tyr(Bn)-Phe-[4-(2-methylaminoethyl)carbamoyl]Pro-Phe-(D,L)[3-(3,8-dimethoxy-naphthalene-2-yl)]Ala-Lys] isomer B,
cyclo[Tyr(Bn)-Phe-[4-(2-aminoethyl)carbamoyl]Pro-Phe-(D,L)[3-(1,4-dimethoxy-naphthalene-2-yl)]Ala-Lys] isomer A,
cyclo[Tyr(Bn)-Phe-[4-(2-aminoethyl)carbamoyl]Pro-Phe-(D,L)[3-(1,4-dimethoxy-naphthalene-2-yl)]Ala-Lys] isomer B,
cyclo[Tyr(Bn)-Phe-[4-(2-aminoethyl)carbamoyl]Pro-Phe-(D)[3-(naphthalene-2-yl)]-Ala-Lys],
cyclo[Tyr(Bn)-Phe-[4-(2-aminoethyl)carbamoyl]Pro-Tyr-(D,L)[3-(3,8-dimethoxy-naphthalene-2-yl)]Ala-Lys] isomer B, and
cyclo[Ser(Bn)-Phe-[4-(2-aminoethyl)carbamoyl]Pro-Phe-(D,L)[3-(3,8-dimethoxy-naphthalene-2-yl)]Ala-Lys] isomer B,
and their salts and pharmaceutically acceptable complexes.

17. The cyclohexapeptide according to claim 5, wherein n is equal to 1.

18. The cyclohexapeptide according to claim 11, wherein the residues 1, 2, and 4-6 are L, and the residue 3 is D.

19. The cyclohexapeptide according to claim 1 in combination with an immunosuppressive agent, with an anti-inflammatory agent, with an agent modulating the secretagogue GH receptor, with an antagonist of the GH receptor, with a secretagogue of the insulin, with a promoter of the insulin secretion, with an insulin sensitiser, with a low insulin dose, with an agent having anti-angiogenic effects or with a chemiotherapy agent.

20. A pharmaceutical composition comprising a cyclohexapeptide according to claim 1 or a pharmaceutically acceptable salt thereof, in association with at least one pharmaceutically acceptable excipient.

21. A process for the preparation of a cyclohexapeptide of claim 1, which comprises the following steps:
a) preparing a linear hexapeptide in which the optional functional groups present in the amino acid side chains are optionally in protected form;
b) cyclising said hexapeptide by means of one or more condensing agents;
c) optionally removing the optional protective groups; and
d) purifying the cyclopeptide thus obtained.

22. The process according to claim 21, wherein the preparation of the linear hexapeptide of point a) is carried out by means of synthesis in solution or in solid phase.

23. The process according to claim 22, wherein the C-terminal amino acid of the linear peptide obtained in point a) is lysine.

24. The process according to claim 22, wherein one of the amino acid residues of the linear peptide obtained in point a) is 4-(2-amino-ethylcarbamoyl-oxy)-proline, protected at the amino group of the side chain.

25. The process according to claim 22, wherein one of the amino acid residues of the linear hexapeptide obtained in point a) is 4-hydroxy-proline with the 4-hydroxyl group unprotected.

26. The process according to claim 25, wherein the 2-amino-ethylcarbamoyl group is bonded to the hydroxyl group of the 4-hydroxy-proline, after the cyclisation stage b), but before the possible removal of the optional protective groups of stage c).

27. The process according to claim 21, wherein the purification according to stage d) is carried out by reverse-phase chromatography and/or by ion-exchange chromatography.

28. A method of treating angiogenesis, proliferative retinopathy, macular edema, disorders correlated to choroidal neovascularisation diseases, vessel graft diseases, vein graft stenoses, restenoses and vascular occulusions following vascular damage, enterocutaneous and pancreatic cutaneous fistulas, irritable intestine syndrome, polycystic kidney disease, rapid gastric emptying syndrome, aqueous diarrhoea syndrome, diarrhoea connected with AIDS, diarrhoea induced by chemotherapy, acute or chronic pancreatitis, gastrointestinal bleeding, comprising administering to patient in need of such treatment a cyclohexapeptide according to claim 1.

29. A method for treating acromegaly comprising administering to a patient in need of such treatment a cyclohexapeptide according to claim 1.

30. A method for treating gastrointestinal hormone-secreting tumours, comprising administering to a patient in need of such treatment a cyclohexapeptide according to claim 1.

31. The method according to claim 30, wherein the gastrointestinal hormone-secreting tumour is a carcinoid tumour.

* * * * *